(12) United States Patent
Bakker et al.

(10) Patent No.: US 11,768,207 B2
(45) Date of Patent: Sep. 26, 2023

(54) DIAGNOSTICS OF PERIODONTITIS BASED ON SALIVARY HGF AND MMP-8

(71) Applicant: KONINKLIJKE PHILIPS N.V., Eindhoven (NL)

(72) Inventors: Bart Jacob Bakker, Eindhoven (NL); Marinus Karel Johannes De Jager, Eindhoven (NL); Amir Hussein Rmaile, Eindhoven (NL); Philip Preshaw, Newcastle upon Tyne (GB); John Taylor, Framlington Place (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 300 days.

(21) Appl. No.: 16/615,429

(22) PCT Filed: May 24, 2018

(86) PCT No.: PCT/EP2018/063737
§ 371 (c)(1),
(2) Date: Nov. 21, 2019

(87) PCT Pub. No.: WO2018/215630
PCT Pub. Date: Nov. 29, 2018

(65) Prior Publication Data
US 2020/0174019 A1  Jun. 4, 2020

(30) Foreign Application Priority Data

May 24, 2017 (EP) ..................................... 17172769
Jan. 15, 2018 (EP) ..................................... 18151632

(51) Int. Cl.
*G01N 33/68* (2006.01)

(52) U.S. Cl.
CPC . *G01N 33/6893* (2013.01); *G01N 2333/4753* (2013.01); *G01N 2333/96494* (2013.01); *G01N 2800/18* (2013.01)

(58) Field of Classification Search
None
See application file for complete search history.

(56) References Cited

U.S. PATENT DOCUMENTS

| 5,736,341 A | 4/1998 | Sorsa |
| 2010/0196941 A1 | 8/2010 | Braun |
| 2017/0007215 A1 | 1/2017 | Podoly |
| 2020/0174019 A1 | 6/2020 | Bakker |

FOREIGN PATENT DOCUMENTS

JP  2003066039 A  3/2003

OTHER PUBLICATIONS

Wilczynska-Borawska M. et al. Hepatocyte Growth Factor in Saliva of Patients with Renal Failure and Periodontal Disease. Renal Failure, 2012; 34(8): 942-951.
Gupta N. et al. Role of salivary matrix metalloproteinase-8 (MMP-8) in chronic periodontitis diagnosis. Front. Med. 2015, 9(1):72-76.
Taylor, John, "Protein Biomarkers of Periodontitis in Saliva", ISRN Inflammation, vol. 141, No. 1, Jan. 2014.
Christodoulides, N. et al., "Lab-on-a-Chip Methods for Point-of-Care Measurements of Salivary Biomarkers of Periodontitis", Annals of the New York Academy of Sciences, vol. 1098, No. 1, Mar. 2007.
Suk, J. et al., "Point-of-care diagnosis of periodontitis using saliva: technically feasible but still a challenge", Frontiers in Cellular and Infection Microbiology, Sep. 2015.
Jaedicke, K. et al., "Salivary cytokines as biomarkers of periodontal diseases", Periodontology 2000, vol. 70, issue 1, Feb. 2016.
Alves, V. et al., "Periodontal Treatment Downregulates Protease-Activated Receptor 2 in Human Gingival Crevicular Fluid Cells", Infection and Immunity, Dec. 2013.
Anil, S. et al., "Hepatocyte Growth Factor Levels in the Saliva and Gingival Crevicular Fluid in Smokers with Periodontitis", Disease Markers, vol. 2014, Article ID 146974, Apr. 2014.
Sorsa, T. et al., "Analysis of matrix metalloproteinases, especially MMP-8, in gingival creviclular fluid, mouthrinse and saliva for monitoring periodontal diseases", Published in Periodontology 2016.
International Search Report and Written Opinion, International Application No. PCT/EP2018/063737, dated Aug. 29, 2018.
Hasan, A. et al., "A clinical guide to periodontology: Pathology of periodontal disease", British Dental Journal vol. 216, pp. 457-461(2014).

(Continued)

*Primary Examiner* — Oluwatosin A Ogunbiyi

(57) ABSTRACT

Disclosed is an in vitro method for assessing whether a human subject has periodontitis. The method comprises detecting, in a sample of saliva from said subject, the concentrations of the proteins Hepatocyte Growth Factor (HGF) and Matrix Metalloproteinase 8 (MMP-8). Based on the concentrations determined, and adding age, and possibly other demographic markers such as sex and/or BMI, a testing value reflecting the joint concentrations is determined for said proteins, in combination with one or more demographic markers. The testing value is compared with a threshold value. The threshold reflects in the same manner the joint concentrations and the age, and possibly other demographic markers, as associated with periodontitis and may be seen as an upper limit of testing values as seen in a population of subjects without periodontitis. Thereby a testing value at or above the threshold value is indicative for periodontitis in said subject.

5 Claims, 2 Drawing Sheets

(56) References Cited

OTHER PUBLICATIONS

Eke, P. et al., "Prevalence of Periodontitis in Adults in the United States: 2009 and 2010", Journal of Dental Research, Aug. 2012.
Thorton-Evans, G. et al., "Periodontitis Among Adults Aged ≥30 Years—United States, 2009-2010", Supplements, Nov. 2013.
Chi, A. et al., "Oral Manifestations of Systemic Disease", Am. Fam. Physician, vol. 82, No. 11, pp. 1381-1388, 2010.
Morgan, R., "Quality evaluation of clinical records of a group of general dental practitioners entering a quality assurance programme", (2001). Brit Dent J 191: 436-41.
Lee, J. et al., "Salivary Diagnostics", Feb. 2009.
Kim, J. et al., "Salivary Biomarkers in the Diagnosis of Periodontal Diseases", J Calif Dent Assoc. Feb. 2013; 41(2): 119-124.
Giannobile, W., "Salivary diagnostics for periodontal diseases", American Dental Association, Oct. 2012.

DIAGNOSTICS OF PERIODONTITIS BASED ON SALIVARY HGF AND MMP-8

This application is the U.S. National Phase application under 35 U.S.C. § 371 of International Application No. PCT/EP2018/063737, filed on 24 May 2018, which claims the benefit of European Application Ser. No. 17172769.6, filed 24 May 2017 and European Application Ser. No. 18151632.9, filed 15 Jan. 2018. These applications are hereby incorporated by reference herein.

FIELD OF THE INVENTION

The invention is in the field of oral care, and pertains to saliva-based diagnostics of periodontal disease. Particularly, the invention pertains to a kit and method for diagnosing periodontitis.

BACKGROUND OF THE INVENTION

Periodontitis is a chronic multifactorial inflammatory disease caused by oral microorganisms and characterized by progressive destruction of the hard (bone) and soft (periodontal ligament) tissues, ultimately leading to tooth mobility and loss. This is to be distinguished from gingivitis which is a reversible infection and inflammation of the gum tissues. Inflammatory periodontitis is one of the most prevalent chronic human diseases and a major cause of adult tooth loss. In addition to the substantial negative impact of periodontitis on oral health, there is also mounting evidence that periodontitis has systemic consequences and that it is a risk factor for several systemic diseases, including heart diseases (e.g. atherosclerosis, stroke), diabetes, pregnancy complications, rheumatoid arthritis and respiratory infections.

Early and accurate diagnosis of periodontal disease, thus, is important from both an oral and overall health perspective.

Periodontal diseases are still poorly diagnosed in general dental practice, resulting in relatively low rates of therapeutic intervention and significant amounts of untreated cases. Current diagnosis relies on imprecise, subjective clinical examination of oral tissue condition (color, swelling, extent of bleeding on probing, probing pocket depth; and bone loss from oral x-rays) by dental professionals. These conventional methods are time consuming, and some of the techniques used (pocket-depth, x-ray) reflect historic events, such as past disease activity, rather than current disease activity or susceptibility to further disease. Hence, more objective, faster, accurate, easier-to-use diagnostics which preferably may also be performed by non-specialists are desirable. Thereby it is desirable to measure current disease activity, and possibly a subject's susceptibility to further periodontal disease.

Saliva or oral fluids have long been advocated as a diagnostic fluid for oral and general diseases, and with the advent of miniaturized biosensors, also referred to as lab-on-chip, point of care diagnostics for rapid chair-side testing have gained greater scientific and clinical interest Especially for periodontal disease detection, inflammatory biomarkers associated with tissue inflammation and breakdown may easily end up in saliva due to proximity, suggesting saliva has strong potential for periodontal disease detection. Indeed, this area thus has gained significant interest and encouraging results have been presented, yet no definite test has emerged yet.

Biomarkers represent biological indicators that underpin clinical manifestations, and as such are objective measures by which to diagnose clinical outcomes of periodontal disease. Ultimately, proven biomarkers could be utilized to assess risk for future disease, to identify disease at the very earliest stages, to identify response to initial therapy, and to allow implementation of preventive strategies.

Previous limitations to the development of point-of-care tests for salivary biomarkers included a lack of technologies that were adaptable to chair-side applications and an inability to analyze multiple biomarkers in individual samples. Also the selection of which multiple biomarkers to include in such a test has not been adequately addressed in the literature nor implemented in practical tests. These challenges are discussed in Taylor J., "Protein Biomarkers of Periodontitis in Saliva" ISRN Inflammation, Vol. 141 No. 1, January 2014.

Gum inflammation, or gingivitis, is a non-destructive periodontal disease caused mainly by the adherence of dental bacterial biofilms, or dental plaque, to the tooth surface. If not detected and treated, the reversible gingivitis usually leads to the inflammation of the tissues surrounding the tooth (i.e. periodontal tissues), a condition defined as periodontitis, and which is irreversible and causes tissue destruction and alveolar bone loss, and ultimately results in the loss of teeth. During the progression of gum disease, there are usually clinical signs and symptoms associated with it, such as the swelling of the gums, the change in color from pink to dark red, the bleeding of the gums, bad breath, and the gums becoming more tender or painful to touch.

It is thus important to assess whether a gingivitis patient has developed periodontitis. Or, to assess whether a treatment of gingivitis has been successful in the sense that the patient has not developed periodontitis. The available methods of making such an assessment, however, involve a labor intensive process that a dentist will not perform routinely on every patient and/or on every visit, and that is impossible to perform by a consumer (self-diagnosis).

It would be desired to provide a simpler process, and particularly a process that requires only that a small saliva sample is taken from a patient, and possibly by the patient him- or herself. It is desired that such a sample be entered into an in vitro diagnostic device, which will allow, based on measurement, a classification of the saliva sample such that it can return an indication of the likelihood that the patient is to be classified as suffering from periodontitis or not.

SUMMARY OF THE INVENTION

In order to better address the foregoing desires, the invention, in one aspect, concerns an in vitro method for assessing whether a human subject has periodontitis, comprising determining the age of the subject and detecting, in a sample of saliva from said human subject, the concentrations of the proteins Hepatocyte Growth Factor (HGF) and Matrix Metalloproteinase 8 (MMP-8); determining a testing value reflecting the joint concentrations determined for said proteins in combination with the age of the subject; comparing the testing value with a threshold value reflecting in the same manner the joint concentrations and the age as associated with periodontitis, so as to assess whether the testing value is indicative for periodontitis in said subject.

In another aspect, the invention presents the use of the proteins HGF and MMP-8 in a saliva sample of a human subject, as well as the age of the human subject, as biomarkers for assessing whether the subject has periodontitis.

In a further aspect, the invention resides in a system for diagnosing periodontitis in a human subject, the system comprising:

means able and adapted to detect in a sample of saliva of the human subject HGF and MMP-8; and a processor able and adapted to determine from the determined concentrations of said proteins, and from demographic information, notably age, an indication whether the patient has periodontitis.

The system optionally contains a data connection to a user interface, particularly a graphical user interface, capable of presenting information, said interface being capable of putting in information on the age of the subject, as well as optionally other information such as sex and/or BMI (Body Mass Index), the interface being either a part of the system or a remote interface.

Optionally one or more of the foregoing items, particularly the processor, are enabled to function "in the cloud", i.e., not on a fixed machine, but by means of an internet-based application.

In a still further aspect, the invention provides a kit for detecting at least two biomarkers for periodontitis in a sample of saliva of a human patient, said kit comprising one or more, typically two, detection reagents, for detecting HGF and MMP-8. Typically, two or more detection reagents are used, each of which binds a different biomarker. In one embodiment, a first detection reagent is capable of binding Hepatocyte growth factor (HGF), and a second detection reagent is capable of binding Matrix Metalloproteinase 8 (MMP-8).

In yet another aspect, the invention provides an in vitro method for determining a change in status of oral health in a human subject over a time interval from a first time point $t_1$ to a second time point $t_2$, the method comprising detecting, in at least one saliva sample obtained from said subject at $t_1$ and in at least one saliva sample obtained from said subject at $t_2$, the concentrations of the proteins: Hepatocyte growth factor (HGF); and Matrix Metalloproteinase 8 (MMP-8), and comparing the concentrations, whereby a difference in any one or both of the concentrations, reflects a change in status.

In a further aspect, the invention provides a method of diagnosing whether a human patient has periodontitis, comprising detecting in a sample of saliva of the human patient the proteins Hepatocyte growth factor (HGF), and Matrix Metalloproteinase 8 (MMP-8), and assessing the presence of periodontitis in the patient on the basis of the concentrations of said proteins in said sample, optionally in combination with the subject's age. Optionally, the method of this aspect comprises the further step of treating the periodontitis in the patient.

In yet a further aspect, the invention provides a method of detecting the proteins Hepatocyte growth factor (HGF) and Matrix Metalloproteinase 8 (MMP-8) in a human patient suffering from periodontitis, comprising:

(a) obtaining a saliva sample from a human patient; and (b) detecting whether Hepatocyte growth factor (HGF) and Matrix Metalloproteinase 8 (MMP-8) are present in the sample by contacting the saliva sample with one or more detection reagents for binding said proteins and detecting binding between each protein and the one or more detection reagents. Typically, there is a first detection reagent capable of binding HGF and a second detection reagent capable of binding Matrix Metalloproteinase 8 (MMP-8). The method may also comprise determining the age of the subject.

DETAILED DESCRIPTION OF THE INVENTION

Figure 1:
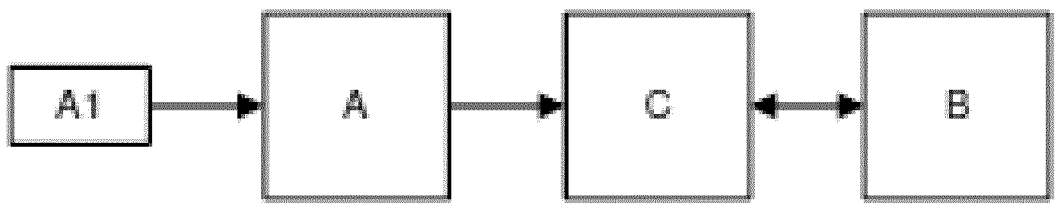
FIG. 1 schematically represents a system for use in the method as described in this disclosure.

In a general sense, the invention is based on the judicious insight that, if also applying age as a biomarker, as few as two proteins can serve as biomarkers in a sample of saliva of a human subject, for assessing with higher accuracy whether said subject has periodontitis. These proteins are Hepatocyte Growth Factor (HGF) and Matrix Metalloproteinase 8 (MMP-8).

HGF is a paracrine cellular growth, motility and morphogenic factor. It is secreted by mesenchymal cells and targets and acts primarily upon epithelial cells and endothelial cells, but also acts on haemopoietic progenitor cells. HGF has been shown to have a major role in myogenesis and in wound healing. Its ability to stimulate mitogenesis, cell motility, and matrix invasion gives it a central role in angiogenesis, tumorogenesis, and tissue regeneration. HGF stimulates growth of epithelial cells and prevents regeneration of the connective tissue attachment. HGF is known as a serum marker indicating disease activity in various diseases.

MMPs are a family of enzymes that are responsible for the degradation of extracellular matrix components such as collagen, proteoglycans, laminin, elastin, and fibronectin. They play a central role in the periodontal ligament (PDL) remodelling, both in physiological and pathological conditions. MMP-8, also known as neutrophil collagenase or PMNL collagenase (MNL-CL), is a collagen protease enzyme which is present in the connective tissue of most mammals.

The proteins mentioned above are known in the art. The skilled person is aware of their structure, and of methods to detect them in an aqueous sample, such as a saliva sample. Hereinafter the aforementioned protein biomarkers are collectively referred to as "the biomarker panels of the invention." A biomarker panel of the invention, in one embodiment, consists of the two protein biomarkers identified in the invention, i.e., HGF and MMP-8, and age. Preferably, the protein biomarkers in a biomarker panel of the invention consist of not more than said two protein biomarkers. In addition to the biomarker panel of the invention, other biomarkers, including protein biomarkers as well as other information, such as further demographic data (e.g., Body Mass Index, sex) can be included in the computation of the biomarker values applied in the present invention. To the extent that these data are not numerical values (such as sex), the skilled person will be able to assign a numerical value to such data (e.g., choosing a "0" for a male and a "1" for a female, or any other discriminating number).

Interesting further protein biomarkers include: Tissue Inhibitor of metalloprotease 1 (TIMP-1); Haemoglobin; Interleukin 1β (IL-1β), CCL-5 (Chemokine (C—C motif) ligand 5, also known as RANTES: regulated upon activation, normal T cell expressed and secreted), Alkaline phosphatase, Elastase (MMP-12), MMP-3, MMP-9, Interleukin-6 (IL-6), C-reactive protein (CRP), Collagen telopeptides, and Albumin.

When other biomarkers are optionally included, the total number of biomarkers (i.e. the biomarker panel of the invention plus additional biomarkers) is typically 4, 5 or 6.

Preferably, the third biomarker is selected from the group consisting of Interleukin 1β (IL-1β), Matrix Metalloproteinase-3 (MMP-3), Haemoglobin, and Interleukin 6 (IL-6).

However, a desirable advantage of the present invention is that the assessment of periodontitis in a subject can be determined by measuring preferably not more than two protein biomarkers, in addition to determining age.

The method, as desired, requires only that a small saliva sample, e.g., a dropsize, is taken from the subject. The size of the sample will typically range of from 0.1 µl to 2 ml, such as 1-2 ml, whereby smaller amounts, e.g., 0.1 to 100 µl can be used for in vitro device processing, and whereby taking a larger sample, such as up to 20 ml, such as 7.5 to 17 ml, is also possible.

This sample is entered into an in vitro diagnostic device, which measures the concentrations of the at least two proteins involved, which is configured to as to receive input reflecting the age of the subject, and which returns a diagnostic outcome, classifying the subject as having periodontitis or not.

The diagnostic outcome is based on comparing the testing value (which is based on, at least, the age of the tested subject and the concentrations of the aforementioned protein biomarkers in a saliva sample of said subject) with a threshold value. The threshold value reflects, in the same manner as for the testing value, the joint protein concentrations as well as age, as associated with periodontitis. Thereby the threshold value can be based, e.g., on testing biomarker values (age and said protein concentrations) in a population of subjects without periodontitis. The threshold value can also be based on the age of a reference patient, and the protein concentrations in a saliva sample of said reference patient, having periodontitis. Similarly, the threshold can be determined on the basis of a group of reference patients. The threshold value can, e.g., also be based on the concentrations of the proteins in a set of samples of saliva obtained from a group of subjects, including subjects that do not have periodontitis and subjects having a known diagnosis of periodontitis, together with the age of said subjects.

The testing value is compared with the threshold value, so as to assess whether the testing value is indicative for periodontitis in said subject. Preferably, the threshold value is determined such that a testing value at or above the threshold value, is indicative for periodontitis in said subject. However, it will be understood that it is also possible to calculate a threshold value (e.g. by using a negative multiplier) such that a testing value indicating periodontitis would be below the threshold, and a testing value indicating no periodontitis, would be above the threshold.

The ease of use of this invention will make it possible to test human subjects, with a desire or need of an assessment of possible periodontitis, on a regular basis (e.g. as part of a regular dental check or even at home). This allows, inter alia, detecting the presence of periodontitis at an early stage, preferably before it is allowed to proceed to an advanced stage of periodontitis, and thus enables more timely taking oral care measures to prevent periodontitis from occurring or advancing. Also, the method can be applied after treatment of a patient previously diagnosed with periodontitis, in order to check whether the periodontitis has been cured. Particularly, the method is also suitable for self-diagnosis, whereby the steps of taking the sample and entering it into a device can be conducted by the subject him- or herself. It is noted that the method of the invention is particularly suitable for a first stage diagnosis of a previously untested subject (e.g. a new patient in a dental clinic). The outcome of the diagnosis will then either be a diagnosis of periodontitis, or a diagnosis of "no periodontitis." In subsequent further tests, a subject diagnosed with periodontitis, can then be further examined so as to assess whether the periodontitis is mild, moderate, or advanced. Similarly, a subject diagnosed as not having periodontitis, can be further examined so as to assess whether the subject, in terms of gum health, is healthy, or whether the subject has initial stages of gum inflammation (i.e., gingivitis, but not periodontitis). The various clinical definitions as acknowledged in the art are discussed below.

A method of the invention typically comprises detecting the aforementioned at least two proteins making up a biomarker panel of the invention, and optional further biomarker proteins, by using one or more detection reagents.

The "saliva" that is tested according to the invention may be undiluted saliva, which may be obtained by spitting or swabbing, or diluted saliva, which may be obtained by rinsing the mouth with a fluid. Diluted saliva may be obtained by the patient rinsing or swilling their mouth for a few seconds with sterile water (for example 5 ml or 10 ml) or other suitable fluid, and spitting into a container. Diluted saliva may sometimes be referred to as an oral rinse fluid.

By "detecting" is meant measuring, quantifying, scoring, or assaying the concentration of the biomarker proteins. Methods of evaluating biological compounds, including biomarker proteins, are known in the art. It is recognized that methods of detecting a protein biomarker include direct measurements and indirect measurements. One skilled in the art will be able to select an appropriate method of assaying a particular biomarker protein.

The term "concentration" with respect to the protein biomarkers is to be given its usual meaning, namely the abundance of the protein in a volume. Protein concentration is typically measured in mass per volume, most typically mg/ml or µg/ml, but sometimes as low as pg/ml. An alternative measure is Molarity (or Molar concentration), mol/L or "M". The concentration can be determined by detecting the amount of protein in a sample of known, determined or pre-determined volume.

An alternative to determining the concentration is to determine the absolute amount of the protein biomarker in the sample, or determining the mass-fraction of the biomarker in the sample, for example the amount of the biomarker relative to the total of all other proteins in the sample.

A "detection reagent" is an agent or compound that specifically (or selectively) binds to, interacts with or detects the protein biomarker of interest. Such detection reagents may include, but are not limited to, an antibody, polyclonal antibody, or monoclonal antibody that preferentially binds the protein biomarker.

The phrase "specifically (or selectively) binds" or "specifically (or selectively) immunoreactive with," when referring to a detection reagent, refers to a binding reaction that is determinative of the presence of the protein biomarker in a heterogeneous population of proteins and other biologics. Thus, under designated immunoassay conditions, the specified detection reagent (e.g. antibody) binds to a particular protein at least two times the background and does not substantially bind in a significant amount to other proteins present in the sample. Specific binding under such conditions may require an antibody that is selected for its specificity for a particular protein. A variety of immunoassay formats may be used to select antibodies specifically immunoreactive with a particular protein. For example, solid-phase ELISA immunoassays (enzyme linked immunosorbent assay) are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice the background signal or noise and more typically more than 10 to 100 times the background.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab')'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region. The antibody may be a bispecific antibody, e.g. an antibody that has a first variable region that specifically binds to a first antigen and a second variable region that specifically binds to a second, different, antigen. Use of at least one bispecific antibody can reduce the number of detection reagents needed.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive.

The biomarker protein(s) of the invention can be detected in a sample by any means. Preferred methods for biomarker detection are antibody-based assays, protein array assays, mass spectrometry (MS) based assays, and (near) infrared spectroscopy based assays. For example, immunoassays, include but are not limited to competitive and non-competitive assay systems using techniques such as Western blots, radioimmunoassays, ELISA, "sandwich" immunoassays, immunoprecipitation assays, precipitin reactions, gel diffusion precipitin reactions, immunodiffusion assays, fluorescent immunoassays and the like. Such assays are routine and well known in the art. Exemplary immunoassays are described briefly below (but are not intended by way of limitation).

Immunoprecipitation protocols generally comprise lysing a population of cells in a lysis buffer such as RIPA buffer (1% NP-40 (nonyl phenoxy polyethoxylethanol) or Triton X-100, 1% sodium deoxycholate, 0.1% SDS (sodium dodecyl sulfate), 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4° C., adding protein A and/or protein G sepharose beads to the cell lysate, incubating for about an hour or more at 4° washing the beads in lysis buffer and re-suspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with Sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise.

ELISAs typically comprise preparing antigen (i.e. the biomarker protein of interest or fragment thereof), coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art.

Since multiple markers are used, a threshold is determined on the basis of the joint concentrations of these protein biomarkers and age. This threshold determines whether a subject is classified as having periodontitis or not. The invention reflects the insight that periodontitis can be detected in human subjects, with sufficient accuracy based on a measurement of the combination of biomarkers (protein biomarkers and age) as indicated above.

This insight supports another aspect of the invention, which is the use of the proteins HGF and MMP-8 in a saliva sample, as well as the age of a patient, as biomarkers of a human subject, for assessing whether the patient has periodontitis.

This use can be implemented in a method as substantially described hereinbefore and hereinafter.

The method of the invention comprises determining a testing value reflecting the joint concentrations measured for said proteins, and the age of the patient. A testing value can be any value obtained by input of the biomarker values, i.e. protein concentrations as determined and age of the subject, and an arithmetic operation of these values. This can, e.g., be a simple addition of these biomarker values. It can also involve multiplying each biomarker value with a factor reflecting a desired weight of these biomarker values, and then adding up the results. It can also involve multiplying the biomarker values with each other, or any combination of multiplication, division, subtraction, exponentiation, and addition. It can further involve, e.g., taking a logarithm of biomarker values or raising biomarker values to some power.

The testing value is compared with a threshold value reflecting in the same manner the biomarker values associated with the presence of periodontitis. Thereby a testing value at or above the threshold is indicative of the presence of periodontitis in the subjects whose saliva is tested.

The threshold value can, e.g., be based on the testing value, obtained in the same manner on the basis of the concentrations determined for the same proteins in a reference sample associated with the presence of periodontitis, i.e. in a patient diagnosed with periodontitis, and of given age. Thereby a value reflecting the same or higher testing value, is indicative of the presence of periodontitis in a tested subject. Analogously, a value reflecting a lower testing value in the saliva of a tested subject, indicates that the patient is not diagnosed as having periodontitis (and may have healthy gums or gingivitis).

The threshold value can also be determined on the basis of measuring the concentrations of the present biomarker proteins in a set of samples, including subjects that do not have periodontitis (and may have healthy gums, or may have gingivitis), and subjects having a known diagnosis of periodontitis, and combining the concentrations with the age of the subjects. Thereby the measured concentration values and the values for age, i.e., the biomarker values can be subjected to statistical analysis, possibly including machine learning methods, allowing to discriminate, with the desired sensitivity and specificity, subjects classified as patients having periodontitis and subjects classified as not having periodontitis. Therefrom, the desired threshold value can be obtained. On the basis of this threshold value, a sample to be tested can be subjected to the same concentration measurement, and determination of age. The concentration and age values are then processed, in the same manner in which the threshold value is obtained, so as to determine a testing value that can be compared with the threshold, thus allowing the tested sample to be classified as indicative of periodontitis or not.

In an interesting embodiment, the testing value is obtained in the form of a score as follows. A numerical value (protein concentration values in e.g. ng/ml and a number for age) is assigned to each measurement, and these values are used in a linear or non-linear combination to calculate a score between zero and one. In the event that the threshold value is determined on the basis of a set of subjects patients as mentioned above, the score between 0 and 1 is typically calculated with the sigmoid function that takes the biomarker values (such as joint concentration and age) as input (as shown further on).

When the score exceeds a certain threshold, the method indicates that the subject has periodontitis. The threshold may be chosen based on the desired sensitivity and specificity.

Clinical definitions as acknowledged in the art are based on the following:

Gingival Index (GI)

A full mouth gingival index will be recorded based on the Lobene Modified Gingival Index (MGI) rated on a scale of 0 to 4, where:

0=absence of inflammation,

1=mild inflammation; slight change in color little change in texture of any portion of but not the entire margin or papillary gingival unit, 2=mild inflammation; but involving entire margin or papillary unit, 3=moderate inflammation; glazing, redness, oedema and/or hypertrophy of margin or papillary unit, 4=severe inflammation; marked redness, oedema and/or hypertrophy of marginal or papillary gingival unit, spontaneous bleeding, congestion, or ulceration].

Probing Depths (PD)

Probing depths will be recorded to the nearest mm using a manual UNC-15 periodontal probe. Probing depth is the distance from the probe tip (assumed to be at the base of the pocket) to the free gingival margin.

Gingival Recession (REC)

Gingival recession will be recorded to the nearest mm using a manual UNC-15 periodontal probe. Gingival recession is the distance from the free gingival margin to the cemento-enamel junction. Gingival recession will be indicated as a positive number and gingival overgrowth will be indicated as a negative number.

Clinical Attachment Loss (CAL)

Clinical attachment loss will be calculated as the sum of probing depth+recession at each site Bleeding on Probing (BOP)

Following probing, each site will be assessed for bleeding on probing, if bleeding occurs within 30 s of probing, a score of 1 will be assigned for the site, otherwise a score of 0 will be assigned.

The resulting subject group (patient group) definition is as follows, whereby the mild-moderate periodontitis group and the advanced periodontitis group are relevant to the present invention:

Healthy group (H): PD≤3 mm in all sites (but would allow up to four 4 mm pockets at distal of last standing molars), no sites with interproximal attachment loss, GI of≥2.0 in≤10% sites, % BOP scores≤10%;

Gingivitis group (G): GI≥3.0 in>30% of sites, no sites with interproximal attachment loss, no sites with PD>4 mm, % BOP scores>10%;

Mild-moderate periodontitis group (MP): interproximal PD of 5-7 mm, (equating to approximately 2-4 mm CAL) at≥8 teeth, % BOP scores>30%;

Advanced periodontitis group (AP): interproximal PD of≥7 mm, (equating to approximately≥5 mm CAL) at≥12 teeth, % BOP scores>30%.

In an embodiment, the method of the invention makes use of a system as represented schematically in FIG. 1. The system can be a single apparatus having various device components (units) integrated therein. The system can also have its various components, or some of these components, as separate apparatuses. The components shown in FIG. 1 are a measurement device (A), a graphical user interface (B) and a computer processing unit (C).

As mentioned above, the system of the invention comprises a data connection to an interface, whereby the interface itself can be a part of the system or can be a remote interface. The latter refers to the possibility to use a different apparatus, preferably a handheld apparatus such as a smartphone or a tablet computer, for providing the actual interface. The data connection in such cases will preferably involve wireless data transfer such as by Wi-Fi or Bluetooth, or by other techniques or standards.

The measurement device (A) is configured to receive a saliva sample, for example by putting a drop of saliva on a cartridge (A1), which can be inserted into the device (A). The device can be an existing device that is capable to determine, from the same saliva sample, the concentrations of at least the proteins HGF and MMP-8, and that is configured to process information on the age of a subject.

The measurement device (A) should be able to receive a saliva sample, for example by putting a drop of saliva on a cartridge (A1), which can be inserted into the device (A). The device may be an existing device that is capable to determine, from the same saliva sample, the concentrations of at least the proteins HGF and MMP-8, and optionally further proteins.

The processing unit (C) receives numerical values for the biomarker values (such as protein concentrations and age) from part (A). The unit (C) is provided with software (typically embedded software) allowing it to calculate a score (S) between 0 and 1. The software further includes a numerical value for the threshold (T). If the calculated value (S) exceeds (T), unit (C) will output an indication (I) of 'periodontitis' to the GUI (B), otherwise it will output 'no periodontitis'). A further embodiment may use the specific value of (S) to indicate the certainty with which the indication (I) is made. This can be a probability score, whereby 0.5 is a possible threshold value, and e.g. a score S=0.8 would indicate the probability of periodontitis. Interesting options are:

Based on the score S, one can directly indicate a certainty, i.e. S=0.8 means 80% certainty of periodontitis;

Based on the score S one can make a binary or tertiary indication:
S<T→no periodontitis (i.e., healthy or gingivitis),
S≥T→periodontitis;
S<R1→no periodontitis, R1≤S<R2→inconclusive,
S≥R2→periodontitis.

In addition, it is possible to attach a certainty to such a binary or tertiary indication. This certainty will be determined by the distance of the score S from the chosen threshold(s) (T,R1,R2).

A specific calculation of the score can be implemented, e.g., by means of a sigmoid function applying the following formula:

$$S = \frac{1}{1 + \exp\left(-\left(c_0 + \sum_{i=1}^{N} c_i B_i\right)\right)}$$

Therein N is the number of proteins/biomarkers used. $c_0$, $c_1$, etc. are coefficients (numerical values) and $B_1$, $B_2$, etc. are the respective biomarker values (such as protein concentrations and age);

*Determining of the coefficients can be done by a training procedure:

Select N1 subjects with periodontitis, and N2 subjects without periodontitis. The subjects without periodontitis are considered to have score S=0, the subjects with periodontitis are considered to have score S=1.

Take a saliva sample from each subject and determine the protein concentrations of a combination of biomarkers as explained above;

Perform logistic regression between the protein concentrations and the scores.

Other regression or machine learning methods (linear regression, neural network, support vector machine) may be used to train a classifier that predicts whether a subject has periodontitis or a non-periodontal diseased oral condition based on the protein concentrations.

With reference to the aforementioned system, the invention also provides, in a further aspect, a system for diagnosing periodontitis in a human subject, the system comprising:

detection means able and adapted to detect in a sample of saliva of a human patient the proteins HGF and MMP-8, and possibly further protein biomarkers as discussed hereinbefore; As explained above, such means are known, and easily accessible to the skilled person. Typically, there is provided a container for receiving an oral sample of a subject therein, the container provided with the detection means;

a processor able and adapted to determine from the determined concentrations of said proteins as well as other information on the subject, notably age, an indication of the subject having periodontitis or not.

Optionally, the system comprises a user interface, particularly a graphical user interface (GUI), capable of presenting information; a GUI is a type of user interface that allows users to interact with electronic devices through graphical icons and visual indicators such as secondary notation, instead of text-based user interfaces, typed command labels or text navigation (none of such interface types being excluded in the present invention); GUIs are generally known, and are used typically in handheld mobile devices such as MP3 players, portable media players, gaming devices, smartphones and smaller household, office and industrial controls; said interface further is capable of putting in information on the age, and preferably also other data such as BMI, of a tested subject.

The invention also provides, either separately or as part of the aforementioned system, a kit for detecting at least two protein biomarkers for periodontitis in a sample of saliva of a human patient, said kit comprising one or more detection reagents for detecting HGF and MMP-8. Typically, the kit comprises twi detection reagents, each detection reagent directed to a different biomarker, wherein a first detection reagent is capable of binding HGF and a second detection reagent is capable of binding MMP-8. As discussed above with reference to the method of the invention, the kit may comprise more detection reagents, for other proteins. In a preferred embodiment the detection reagents made available in the kit consist of the detection reagent s for the selection of two proteins making up a two-protein biomarker panel of the invention, as mentioned.

Preferably said kits comprise a solid support, such as a chip, a microtiter plate or a bead or resin comprising said detection reagents. In some embodiments, the kits comprise mass spectrometry probes, such as ProteinChip™.

The kits may also provide washing solutions and/or detection reagents specific for either unbound detection reagent or for said biomarkers (sandwich type assay).

In an interesting aspect, the recognition of a biomarker panel of the invention is applied in monitoring the status of possible periodontitis in a human subject, over time. Accordingly, the invention also provides an in vitro method for determining a change in status of oral health in a human subject over a time interval from a first time point $t_1$ to a second time point $t_2$, the method comprising detecting, in at least one sample of saliva obtained from said subject at $t_1$ and in at least one sample of saliva obtained from said patient at $t_2$, the concentrations of the proteins HGF and MMP-8, and comparing the concentrations, whereby a difference in both concentrations reflects a change in status. This difference can be reviewed as a difference in concentrations, thus allowing a direct comparison without first generating a number between 0 and 1, or any other classification. It will be understood that the measurements received at both points in time can also be processed in just the same manner as done when determining the assessment of periodontitis as above.

The invention also provides a method of diagnosing whether a human patient has periodontitis, comprising detecting in the patient's saliva the presence of the proteins HGF and MMP-8, and assessing the presence of periodontitis in the patient on the basis of the concentrations of said proteins in said sample and the age of the subject. Optionally, the method of this aspect comprises the further step of treating the periodontitis in the patient. This optional treatment step can comprise the administration of known therapeutic agents or dental procedures, or a combination of therapeutic agents and dental procedures. Known therapeutic agents include the administration of antimicrobial-containing agents such as a mouthwash, chip, gel or microsphere. A typical antimicrobial agent for use in treating periodontitis is chlorhexidine. Other therapeutic agents include antibiotics, typically orally-administered antibiotics, and enzyme suppressants such as doxycycline. Known non-surgical therapeutic procedures include scaling, or scaling and root planing (SRP).

The invention further provides a method of detecting the proteins HGF and MMP-8 in a patient suffering from periodontitis, comprising:

(a) obtaining a saliva sample from a human patient; and (b) detecting whether HGF and MMP-8 are present in the saliva sample by contacting the saliva sample with one or more detection reagents capable of binding said proteins and detecting binding between each protein and the one or more detection reagents. The age of the patient is also typically determined.

The invention will be further illustrated with reference to the following non-limiting experimental information.

It was found that accurate diagnostic results are obtained with biomarker panels including both HGF and MMP-8.

Figure 2:
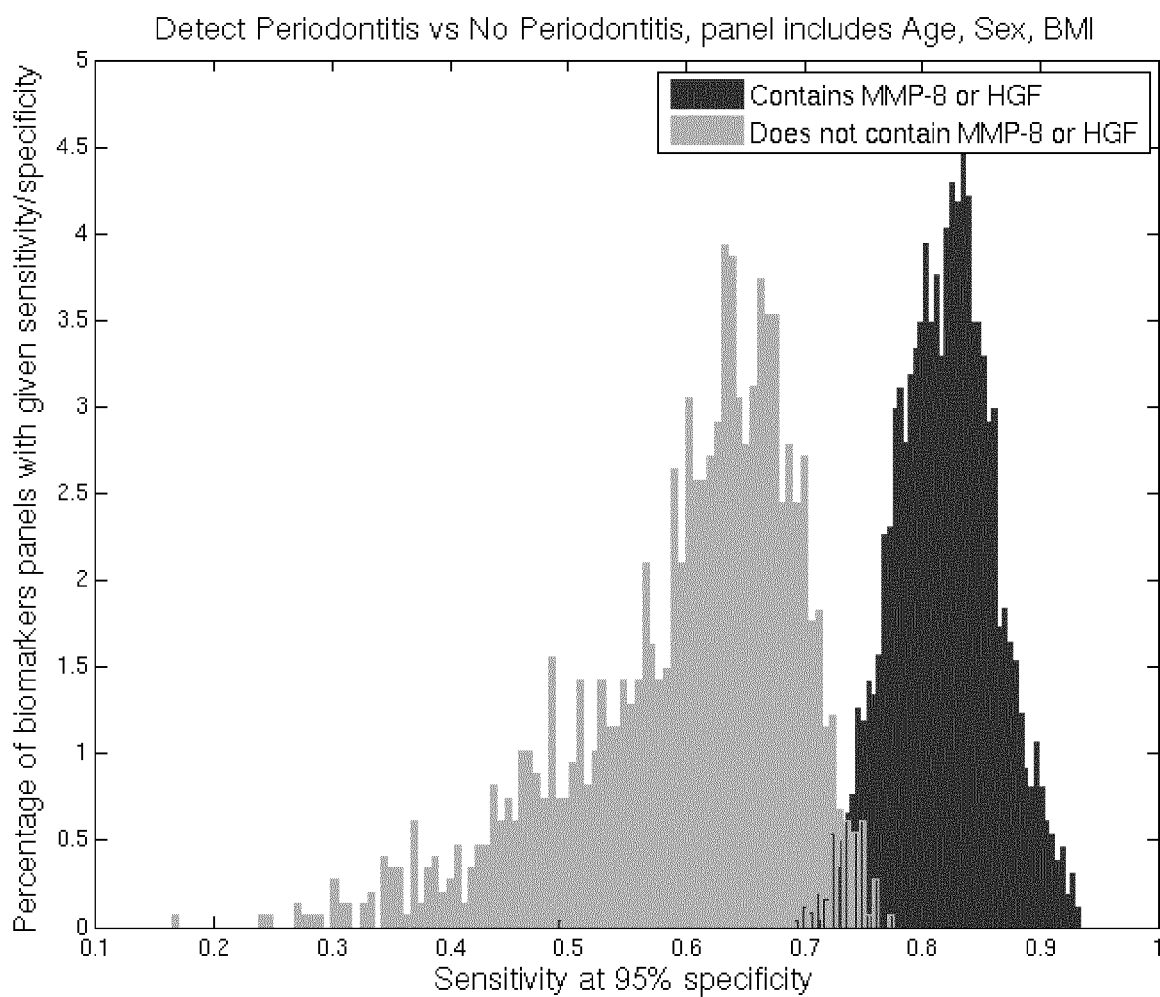
FIG. 2 is a graph wherein the percentage of defined biomarker panels is plotted against the sensitivity for periodontitis at 95% specificity.

HGF and MMP-8 are both shown to be promising biomarkers for determining whether a subject has a periodontal disease with relative high expression levels of both detected in saliva samples of test subjects with a periodontal disease and relative low expression levels of both detected in oral samples of test subjects with periodontal health. The sensitivity of biomarker panels including HGF and/or MMP-8 for periodontitis are shown in FIG. 2. This figure shows the sensitivity at 95% specificity.

FIG. 2 shows that the biomarker or biomarker panels comprising age, sex and BMI of the subject and at least one of HGF and MMP-8 have a distinct higher sensitivity at 95% specificity for periodontitis as compared to biomarkers or panels having none of said two protein biomarkers.

Figure 3:
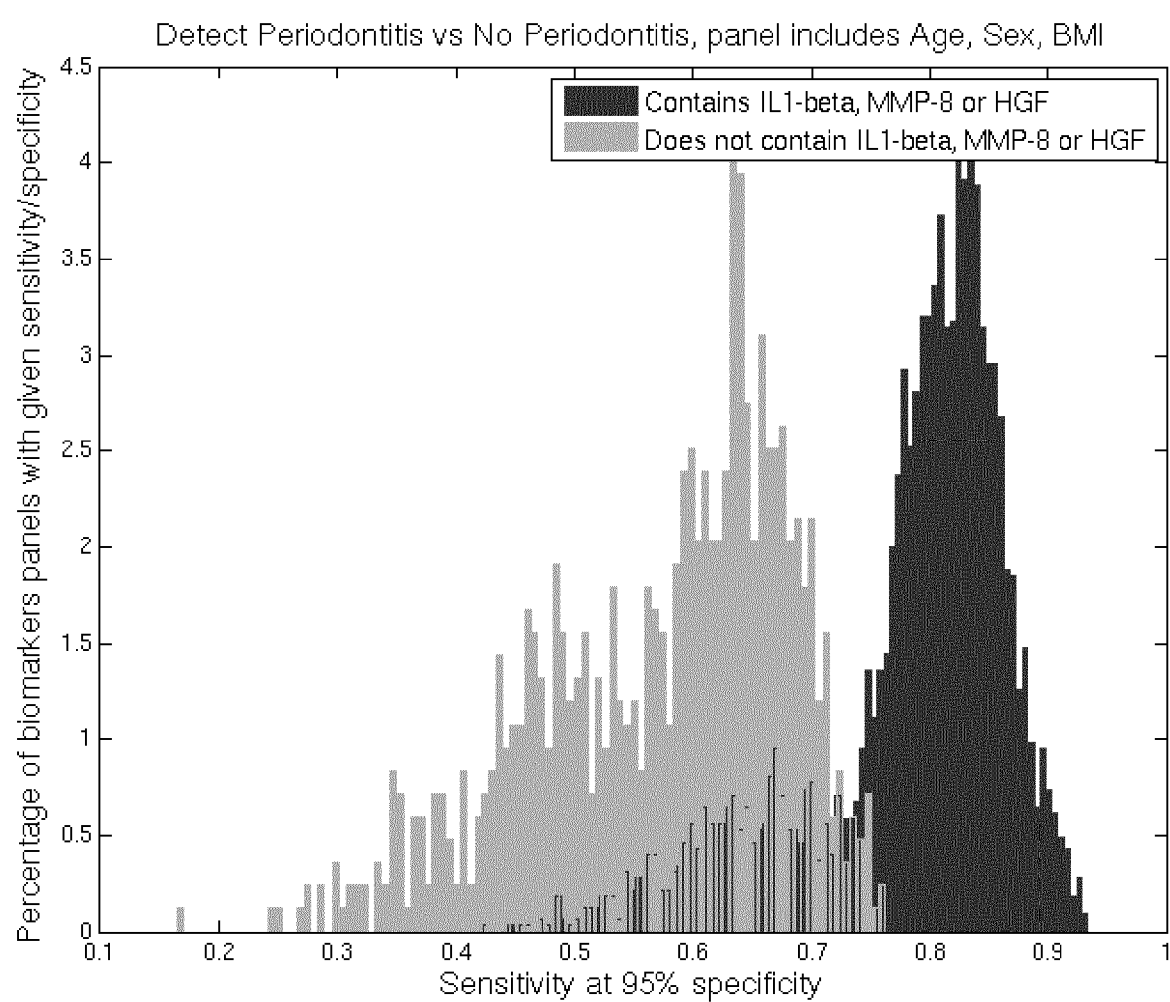
FIG. 3 is a similar graph as FIG. 2, for different biomarker panels.

FIG. 3 shows that the biomarker or biomarker panels comprising age, sex and BMI of the subject and at least one of HGF, MMP-8 and IL-1β have a distinct higher sensitivity at 95% specificity for periodontitis as compared to biomarkers or panels having none of said protein biomarkers. The resemblance between the figures FIG. 2 and FIG. 3 supports the relevance of either HGF or MMP-8 as biomarker for diagnosing periodontitis.

It is found that both HGF and MMP-8 as single biomarker demonstrate a high sensitivity at 95% specificity for detecting periodontitis in a subject based additionally on age, sex and BMI of the subject, see table 2.

TABLE 1

| Single biomarker sensitivity at 95% specificity for periodontitis. | |
| --- | --- |
| MMP-8 | 0.91 |
| HGF | 0.83 |
| MMP-9 | 0.71 |
| MMP-3 | 0.52 |
| Haemoglobin | 0.52 |
| Elastase | 0.50 |
| IL-1b | 0.49 |
| CRP | 0.37 |
| IL-6 | 0.36 |
| Albumin | 0.33 |
| RANTES | 0.31 |
| TIMP-1 | 0.26 |
| Collagen Telopeptides | 0.16 |

Despite such results for the single biomarkers HGF and MMP-8, biomarker panels including at least two biomarkers and preferably three or more biomarkers are more suited for accurately diagnosing a periodontal disease, as one biomarker may not be a sufficiently reliable source for specifying the pathogenesis of the particular disease. For example the single biomarker may be highly specific and sensitive for a plurality of different diseases, hence resulting in less accurate predictions of a subject having a specific disease of said plurality of diseases. The use of combinations of biomarkers provides additive and powerful diagnostic information.

In the method according to the invention an expression of at least HGF and MMP-8 is thus determined in a saliva sample of a subject. As shown in table 3 the best two-biomarker panel of all the panels tested as shown in FIGS. 2 and 3 is the combination of HGF and MMP-8. Like table 2 for the single biomarkers, table 3 shows the sensitivity of the two-biomarker panels including HGF and the indicated proteins at 95% specificity for detecting periodontitis in a subject based additionally on age, sex and BMI of the subject.

Table 4 additionally shows the relevance of MMP-8 as compared to the other indicated proteins, as evidenced by the distinct lower score of 0.8333 for the best remaining biomarker panel without HGF and MMP-8.

TABLE 2

| Biomarker panel sensitivity at 95% specificity for periodontitis for panels consisting of HGF and the indicated protein. | |
| --- | --- |
| IL-1b: | 0.83 |
| Albumin: | 0.76 |
| Haemoglobin: | 0.81 |
| Elastase: | 0.77 |
| IL-6: | 0.83 |
| MMP-8: | 0.90 |
| TIMP-1: | 0.76 |
| MMP-9: | 0.82 |
| RANTES: | 0.83 |
| MMP-3: | 0.83 |
| CRP: | 0.75 |

TABLE 3

Biomarker panel sensitivity at 95% specificity for periodontitis for biomarker panels based additionally on age, sex and BMI of subject. The middle column indicates the score for the best biomarker panel including HGF and at least one of the indicated proteins. The right column indicates the score for the best biomarker panel without HGF and the indicated protein.

| | | |
|---|---|---|
| IL-1b: | 0.9203 | 0.9155 |
| Albumin: | 0.9203 | 0.9155 |
| Haemoglobin: | 0.9203 | 0.9127 |
| Elastase: | 0.9203 | 0.9155 |
| IL-6: | 0.9203 | 0.8928 |
| MMP-8: | 0.9203 | 0.8333 |
| TIMP-1: | 0.9203 | 0.9155 |
| MMP-9: | 0.9203 | 0.9114 |
| RANTES: | 0.9203 | 0.9114 |
| MMP-3: | 0.9203 | 0.9041 |
| CRP: | 0.9203 | 0.9155 |

In a preferred embodiment of the method according to the invention for diagnosing periodontitis the method comprises that in addition to MMP-8 and HGF the expression of at least a third biomarker is determined, the third biomarker being one or more selected from the group of biomarkers consisting of Interleukin 1β (IL-1β), Matrix Metalloproteinase-3 (MMP-3), Haemoglobin, and Interleukin 6 (IL-6).

While the invention has been illustrated and described in detail in the drawings and foregoing description, such illustration and description are to be considered illustrative or exemplary and not restrictive; the invention is not limited to the disclosed embodiments.

For example, it is possible to present binding agents for different biomarkers in different units. Or, conveniently, a kit of the invention can comprise a fixed set of binding agents for the protein biomarkers that are used in all embodiments, i.e., HGF and MMP-8, and flexible modules comprising a binding agent for one or more further biomarkers, such as IL-1β.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In sum, we hereby disclose an in vitro method for assessing whether a human subject has periodontitis. The method comprises detecting, in a sample of saliva from said subject, the concentrations of the proteins Hepatocyte Growth Factor (HGF) and Matrix Metalloproteinase 8 (MMP-8). Based on the concentrations determined, and adding age, and possibly other demographic markers such as sex and/or BMI, a testing value reflecting the joint concentrations determined for said proteins, in combination with the one or more demographic marker, is calculated. The testing value is compared with a threshold value. The threshold reflects in the same manner the joint concentrations and the age, and possibly other demographic markers, as associated with periodontitis, and may be seen as an upper limit, or of testing values as seen in a population of subjects without periodontitis. The upper limit can also be the 95% quantile, or a similar measure so as to exclude outliers.

Thereby a testing value at or above the threshold value is indicative for periodontitis in said subject.

The invention claimed is:

1. A method for treating a human subject diagnosed with periodontitis, comprising:
    determining the age of the human subject and detecting, in a sample of saliva from said human subject, the concentrations of proteins consisting of Hepatocyte Growth Factor (HGF) and Matrix Metalloproteinase 8 (MMP-8);
    determining a single testing value for the human subject comprising a combination of the determined concentrations of HGF and MMP-8 and the determined age of the subject;
    comparing the determined testing value with a threshold value, the threshold value reflecting in the same manner the joint combined concentrations of HGF and MMP-8 and the age as associated with periodontitis;
    determining, based on the comparison, that the testing value is indicative for periodontitis in said human subject; and
    administering, in response to determining that the human subject has periodontitis, a treatment comprising a dental procedure and/or administration of an anti-periodontitis therapeutic agent.

2. A method according to claim 1, wherein:
    a) the threshold value is based on testing values as seen in a population of subjects without periodontitis; or
    b) the threshold value is based on the concentrations determined for the proteins in a reference sample associated with the presence of periodontitis; or
    c) the threshold value is based on the concentrations of the proteins in a set of samples, including subjects that do not have periodontitis and subjects having a known diagnosis of periodontitis.

3. A method according to claim 1, wherein the determined concentration values of HGF and MMP-8 are arithmetically processed into a number between 0 and 1.

4. An in vitro method for determining a change in status of oral health in a human subject over a time interval from a first time point $t_1$ to a second time point $t_2$, the method comprising:
    detecting, in at least one sample of saliva obtained from said subject at $t_1$ and in at least one sample of saliva obtained from said patient at $t_2$, the concentrations of proteins consisting of Hepatocyte Growth Factor (HGF) and Matrix Metalloproteinase 8 (MMP-8), and
    comparing the concentrations determined at $t_1$ and at $t_2$, whereby a difference in both concentrations reflects a change in status of oral health of the human subject, the change in status comprising an indication that the human subject has periodontitis at $t_2$; and
    administering, in response to determining that the human subject has periodontitis at $t_2$, a treatment comprising a dental procedure and/or administration of an anti-periodontitis therapeutic agent.

5. A method for treating a subject diagnosed with periodontitis, comprising:
    receiving a diagnosis of periodontitis for the subject, the diagnosis comprising a result of comparison of a testing value to a threshold value, wherein the diagnosis is made by:
        determining the age of the subject and detecting, in a sample of saliva from said subject, the concentrations of proteins consisting of Hepatocyte Growth Factor (HGF) and Matrix Metalloproteinase 8 (MMP-8);

determining a single testing value for the subject comprising a combination of the determined concentrations of HGF and MMP-8 and the determined age of the subject; and comparing the determined testing value with a threshold value, the threshold value reflecting in the same manner the joint combined concentrations of HGF and MMP-8 and age as associated with periodontitis;

diagnosing, based on the comparison where the testing value exceeds the threshold value, that the subject has periodontitis; and administering, in response to receiving the diagnosis of periodontitis for the subject, a treatment comprising a dental procedure and/or administration of an anti-periodontitis therapeutic agent.

* * * * *